US00PP32072P3

(12) United States Plant Patent
van den Haak

(10) Patent No.: US PP32,072 P3
(45) Date of Patent: Aug. 11, 2020

(54) ***HEUCHERA* PLANT NAMED 'IFHEHB'**

(50) Latin Name: *Heuchera hybrida*
Varietal Denomination: IFHEHB

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 16/501,903

(22) Filed: Jul. 1, 2019

(65) Prior Publication Data

US 2020/0022298 P1 Jan. 16, 2020

Related U.S. Application Data

(60) Provisional application No. 62/764,038, filed on Jul. 13, 2018.

(51) Int. Cl.
*A01H 5/12* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC . A01H 5/02; A01H 5/12; A01H 5/025; A01H 6/80
See application file for complete search history.

*Primary Examiner* — June Hwu
(74) *Attorney, Agent, or Firm* — C. A. Whealy

(57) ABSTRACT

A new and distinct cultivar of *Heuchera* plant named 'IFHEHB', characterized by its compact and uniformly mounded plant habit; relatively rapid growth rate; densely foliated and bushy appearance; silvery purple-colored leaves; long flowering period; numerous inflorescences with sterile light red purple-colored flowers; and good garden performance and winter hardiness.

2 Drawing Sheets

Botanical designation: *Heuchera hybrida.*
Cultivar denomination: 'IFHEHB'.

BACKGROUND OF THE INVENTION

The present invention relates to a new and distinct *Heuchera* plant, botanically known as *Heuchera hybrida*, typically grown as a landscape *Heuchera* and hereinafter referred to by the name 'IFHEHB'.

The new *Heuchera* plant is a product of a planned breeding program conducted by the Inventor in Andijk, The Netherlands. The objective of the breeding program is to create new compact *Heuchera* plants with attractive leaf and flower coloration and good garden performance.

The new *Heuchera* plant originated from an open-pollination of a proprietary selection of *Heuchera hybrida* identified as code number 083-11-K016-02, not patented, as the female, or seed, parent with an unknown proprietary selection of *Heuchera hybrida* as the male, or pollen, parent in June, 2013. The new *Heuchera* plant was discovered and selected as a single plant from within the progeny of the stated open-pollination in a controlled nursery environment in Andijk, The Netherlands in July, 2014.

Asexual reproduction of the new *Heuchera* plant by in vitro meristem culture in a controlled environment in Andijk, The Netherlands since September, 2016 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFHEHB'. These characteristics in combination distinguish 'IFHEHB' as a new and distinct *Heuchera* plant:

1. Compact and uniformly mounded plant habit.
2. Relatively rapid growth rate.
3. Densely foliated and bushy appearance.
4. Silvery purple-colored leaves.
5. Long flowering period.
6. Numerous inflorescences with sterile light red purple-colored flowers.
7. Good garden performance and winter hardiness.

Plants of the new *Heuchera* differ primarily from plants of the female parent selection in leaf color as plants of the new *Heuchera* have more silvery-colored leaves than plants of the female parent selection. In addition, plants of the new *Heuchera* differ from plants of the female parent selection in flower color as plants of the new *Heuchera* have light red purple-colored flowers whereas flowers of plants of the female parent selection have white-colored flowers.

Plants of the new *Heuchera* can be compared to plants of *Heuchera hybrida* 'Sugar Plum', disclosed in U.S. Plant Pat. No. 21,857. In side-by-side comparisons, plants of the new *Heuchera* differ primarily from plants of 'Sugar Plum' in the following characteristics:

1. Plants of the new *Heuchera* are more compact than plants of 'Sugar Plum'.
2. Plants of the new *Heuchera* have smaller leaves than plants of 'Sugar Plum'.

3. Plants of the new *Heuchera* have silvery purple-colored leaves whereas plants of 'Sugar Plum' have deep red purple to silver-colored leaves.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet is a side perspective view of a typical flowering plant of 'IFHEHB' grown in a container.

The photograph at the top of the second sheet is a close-up view of typical leaves of 'IFHEHB'.

The photograph at the bottom of the second sheet is a close-up view of a typical inflorescence of 'IFHEHB'.

DETAILED BOTANICAL DESCRIPTION

The aforementioned photographs and following observations, measurements and values describe plants grown during the summer with three plants in a 15-cm containers in an outdoor nursery in Heerhugowaard, The Netherlands and under cultural practices typical of commercial *Heuchera* production. During the production of the plants, day temperatures ranged from 10° C. to 25° C. and night temperatures ranged from 4° C. to 15° C. Plants were 18 weeks old when the photographs and the description were taken. In the following description, color references are made to The Royal Horticultural Society Colour Chart, 2015 Edition, except where general terms of ordinary dictionary significance are used.

Botanical classification: *Heuchera hybrida* 'IFHEHB'.

Parentage:

*Female, or seed, parent*.—Proprietary selection of *Heuchera hybrida* identified as code number 083-11-K016-02, not patented.

*Male, or pollen, parent*.—Unknown proprietary selection of *Heuchera hybrida*, not patented.

Propagation:

*Type*.—By in vitro meristem culture.

*Time to initiate roots, summer*.—About ten days at temperatures about 22° C.

*Time to initiate roots, winter*.—About 15 days at temperatures about 20° C.

*Time to produce a rooted young plant, summer*.—About 42 days at temperatures about 20° C.

*Time to produce a rooted young plant, winter*.—About 50 days at temperatures about 20° C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; basal rosette plant habit with leaves developing from the base; densely foliated and dense and bushy appearance; compact and uniformly mounded plant habit; overall shape, flattened globular with upright inflorescences held above the foliar plane; moderately vigorous growth habit; moderate growth rate.

*Plant height, soil level to top of foliar plane*.—About 23.2 cm.

*Plant height, soil level to top of inflorescences*.—About 55.6 cm.

*Plant diameter or spread*.—About 68.2 cm.

Leaf description:

*Arrangement*.—Alternate in basal rosettes; simple.

*Length*.—About 12.8 cm.

*Width*.—About 11.9 cm.

*Shape*.—Broadly ovate; palmately lobed.

*Apex*.—Obtuse with a small and short abruptly acute tip.

*Base*.—Hastate, lobes touching to slightly imbricate.

*Margin*.—About seven lobes per leaf; crenate with small and short abruptly acute tips; sinuses shallow to medium in depth and divergent; slightly undulate.

*Texture and luster, upper surface*.—Sparsely pubescent; matte.

*Texture and luster, lower surface*.—Sparsely pubescent; slightly rugose; glossy.

*Venation pattern*.—Palmate; reticulate.

*Color*.—Developing leaves, upper surface: Close to N187B with a silvery sheen; venation, close to 187B. Developing leaves, lower surface: Close to 187B; venation, close to 187C to 187D. Fully expanded leaves, upper surface: Close to N187B with a silvery sheen; venation, close to between N186A and 203A. Fully expanded leaves, lower surface: Close to 187A; venation, close to N77B.

*Petioles*.—Length: About 18.8 cm. Diameter: About 2.5 mm. Strength: Moderately strong. Texture and luster, upper and lower surfaces: Densely pubescent; slightly glossy. Color, upper surface: Close to between N186C and 200A. Color, lower surface: Close to 187A to 187B.

*Stipules*.—Quantity and arrangement: One at the base of each leaf. Length: About 1.6 cm. Width: About 4 mm. Shape: Lanceolate with acute apex. Color, upper and lower surfaces: Close to 71A.

Flower description:

*Flower type and flowering habit*.—Single campanulate flowers arranged on axillary compound spikes; each spike with about 125 flowers; about 1,250 flowers develop per plant during the flowering season; flowers face outwardly to slightly nodding.

*Fragrance*.—None detected.

*Time of flowering*.—Plants flower continuously from the late spring into the summer in The Netherlands; plants begin flowering about four months after planting.

*Inflorescence longevity*.—Individual flowers last about a week on the plant; flowers not persistent.

*Inflorescence length*.—About 27.3 cm.

*Inflorescence width*.—About 7.6 cm.

*Flower diameter*.—About 4 mm.

*Flower depth (height)*.—About 6 mm.

*Flower buds*.—Height: About 5 mm. Diameter: About 2 mm. Shape: Elliptic. Texture and luster: Densely pubescent; matte. Color: Close to 180B; distally, close to 182D and proximally, close to 183A.

*Petals*.—Quantity and arrangement: Five petals in a single whorl. Length: About 3 mm. Width: About 1 mm. Shape: Oblanceolate. Apex: Acute. Base: Narrow attenuate. Margin: Entire. Texture and luster, upper surface: Smooth, glabrous; matte. Texture and luster, lower surface: Sparsely pubescent; matte. Color: When opening, upper and lower surfaces: Close to NN155D; distally, tinged with close to 75C. Fully opened, upper and lower surfaces: Close to NN155D; distally, tinged with close to 75C; venation, similar to lamina color; color does not change with development.

*Sepals*.—Quantity and arrangement: Five sepals in a single whorl; lower 40% fused. Length: About 5 mm. Width: About 1.75 mm. Shape: Ovate. Apex: Obtuse. Margin: Entire. Texture and luster, upper surface: Smooth, glabrous; matte. Texture and luster, lower surface: Densely pubescent; matte. Color: When opening, upper surface: Close to 65C. When opening, lower surface: Close to 60C and 60D; proximally, close to 183A. Fully opened, upper surface: Close to 65C. Fully opened, lower surface: Proximally, close to 183A; mid-section, close to 65C; distally, close to 60B.

*Peduncles*.—Length: About 53.1 cm. Diameter: About 2 mm. Strength: Moderately strong. Aspect: Erect to about 45° from vertical. Texture and luster: Densely pubescent; glossy. Color: Close to between N186C and 200A.

*Pedicels*.—Length: About 4 mm. Diameter: About 0.5 mm. Strength: Moderately strong. Aspect: About 30° from peduncle axis. Texture and luster: Moderately to densely pubescent; slightly glossy. Color: Close to between N186C and 200A.

*Reproductive organs*.—Androecium: Stamen number: Five per flower. Filament length: About 3 mm. Filament color: Close to NN155A. Anther size: About 0.5 mm by 0.5 mm. Anther shape: Deltoid. Anther color: Close to 24B. Amount of pollen: Scarce. Pollen color: Close to 10B. Gynoecium: Pistil number: Two per flower. Pistil length: About 4 mm. Style length: About 3.75 mm. Style color: Close to 181A; proximally, close to 146C. Stigma diameter: About 0.2 mm. Stigma shape: Club-shaped. Stigma color: Close to 157A. Ovary color: Close to 146C.

*Seeds and fruits*.—To date, seed and fruit development have not been observed on plants of the new *Heuchera*.

Pathogen & pest resistance: To date, plants of the new *Heuchera* have not been observed to be resistant to pathogens and pests common to *Heuchera* plants.

Garden performance: Plants of the new *Heuchera* have been observed to have good garden performance and to tolerate high temperatures about 35° C. and to be suitable for USDA Hardiness Zones 3 through 9.

It is claimed:

1. A new and distinct *Heuchera* plant named 'IFHEHB' as illustrated and described.

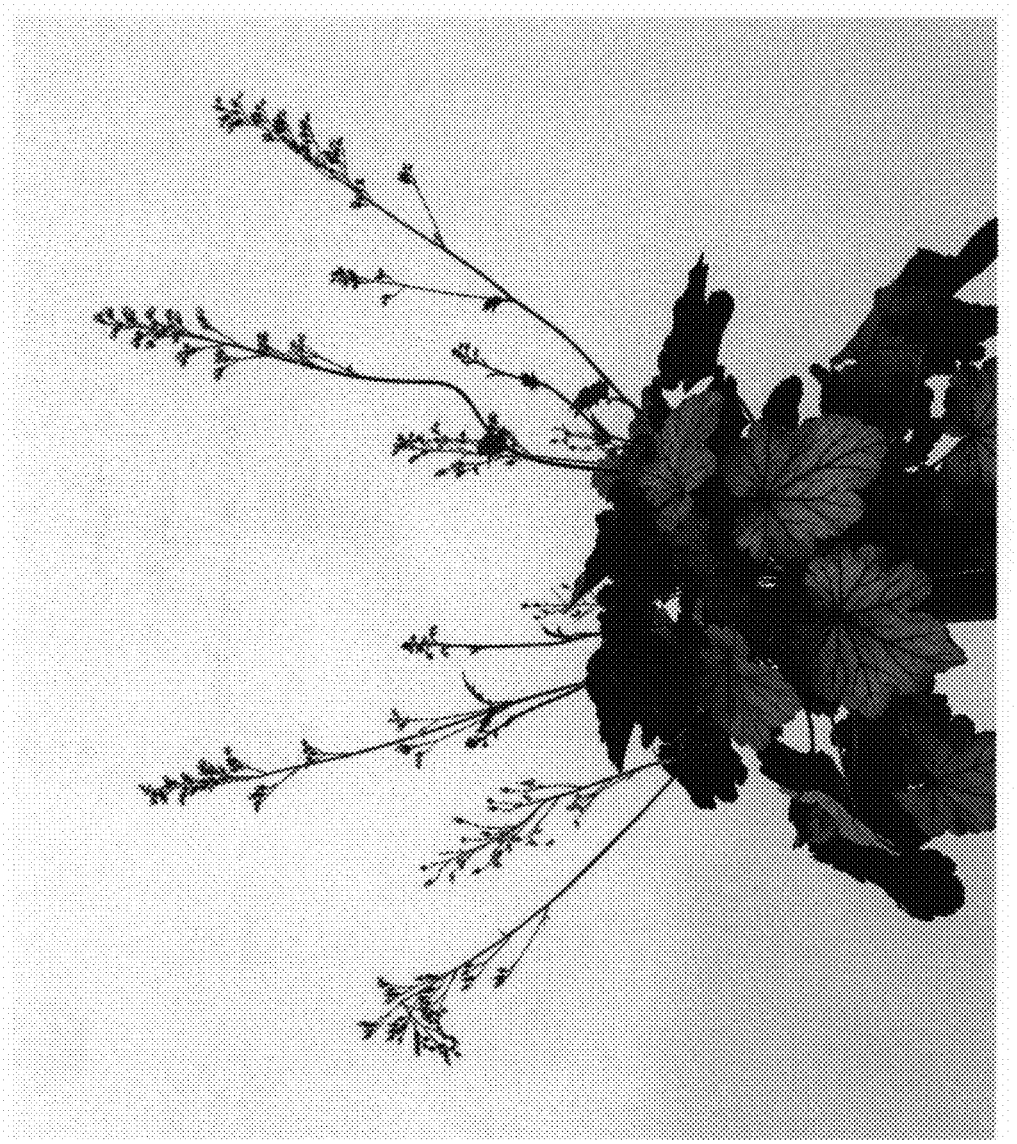

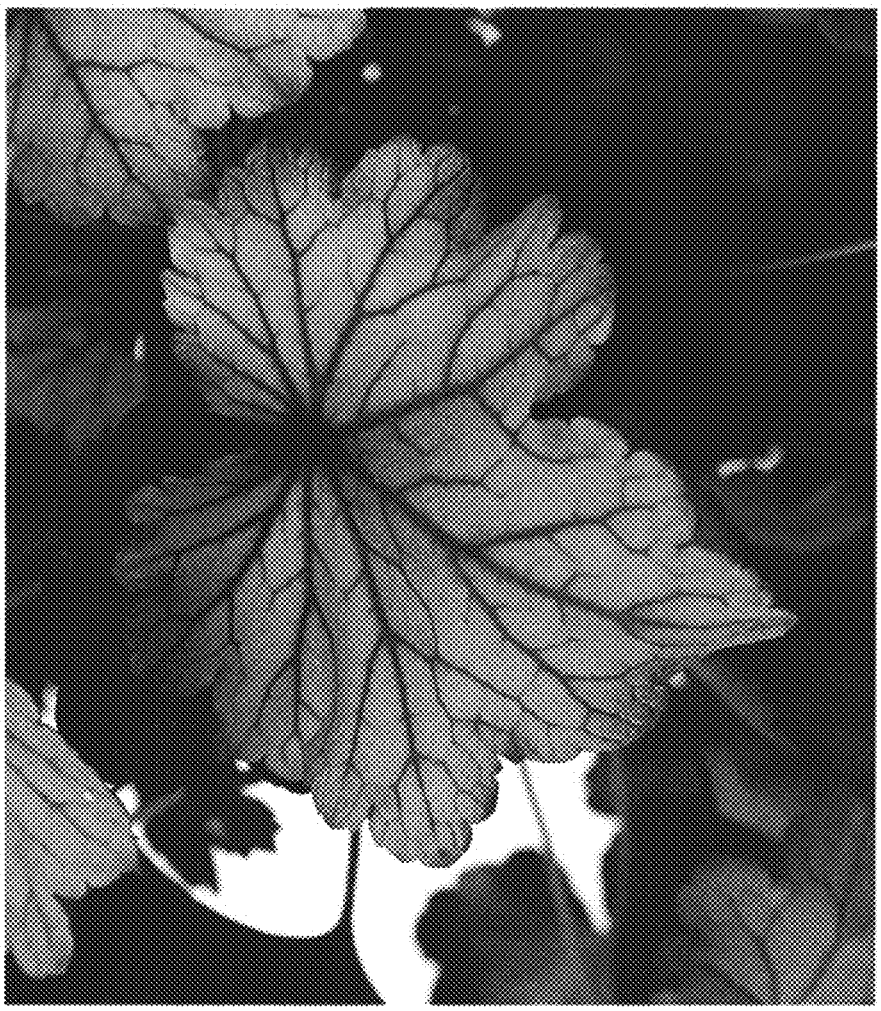
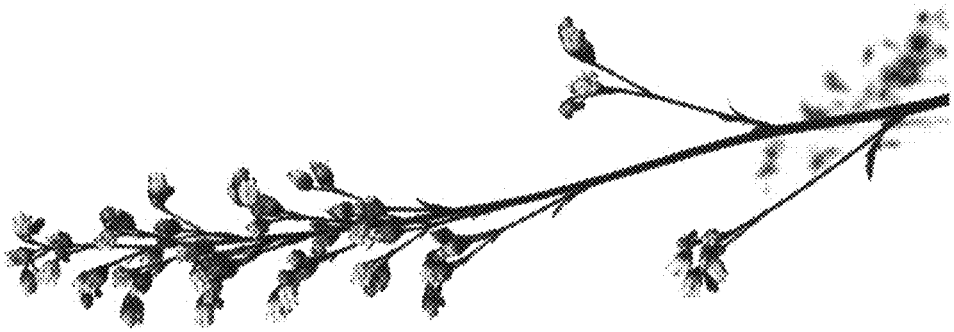

* * * * *